United States Patent [19]

Ho et al.

[11] Patent Number: 4,506,015

[45] Date of Patent: Mar. 19, 1985

[54] MULTI-LAYER IMMOBILIZED ENZYME COMPOSITIONS

[75] Inventors: Guan-Huei Ho; Chiang-Chang Liao, both of Tillsonburg, Canada

[73] Assignee: Borden Company Limited, Ontario, Canada

[21] Appl. No.: 435,218

[22] Filed: Oct. 19, 1982

Related U.S. Application Data

[63] Continuation of Ser. No. 148,012, May 8, 1980, abandoned.

[51] Int. Cl.³ .................. C12N 11/18; C12N 11/14; C12N 9/38; C12N 9/92
[52] U.S. Cl. ..................... 435/175; 435/176; 435/207; 435/234
[58] Field of Search ............... 435/174, 175, 176, 177, 435/180, 181, 207, 234

[56] References Cited

U.S. PATENT DOCUMENTS

| | | | |
|---|---|---|---|
| 3,519,538 | 7/1970 | Messing et al. | 435/176 |
| 3,556,945 | 1/1971 | Messing | 435/176 |
| 3,639,558 | 2/1972 | Csizmas et al. | 435/177 |
| 3,666,627 | 5/1972 | Messing | 435/176 |
| 3,669,841 | 6/1972 | Miller | 435/176 |
| 3,715,278 | 2/1973 | Miller | 435/176 |
| 3,741,871 | 6/1973 | Weeks et al. | 435/181 |
| 3,767,531 | 10/1973 | Olson et al. | 435/181 |
| 3,783,101 | 1/1974 | Tomb et al. | 435/176 |
| 3,796,634 | 3/1974 | Haynes et al. | 435/176 |
| 3,830,699 | 8/1974 | Zaborsky | 435/181 |
| 3,836,433 | 9/1974 | Wirth et al. | 435/181 |
| 3,841,971 | 10/1974 | Messing | 435/176 |
| 3,852,496 | 12/1974 | Weetall et al. | 435/176 |
| 4,004,979 | 1/1977 | Avrameas et al. | 435/175 |
| 4,204,040 | 5/1980 | Keyes | 435/175 |
| 4,229,536 | 10/1980 | DeFilippi | 435/176 |

OTHER PUBLICATIONS

Messing, R. A., Immobilized Enzymes For Industrial Reactors, Academic Press, N.Y., 1975 (pp. 91–95).
Olson et al., *J. Ag. Food Chem.* 21, 440 (1973).

*Primary Examiner*—David M. Naff
*Attorney, Agent, or Firm*—Robbins & Laramie

[57] ABSTRACT

A high activity immobilized enzyme composite is prepared by covalently bonding a second enzyme layer to a first enzyme layer that is immobilized to a carrier. The carrier is preferably silica gel which has been activated by treatment with a strong base followed by treatment with a strong acid. The first enzyme layer is covalently bonded to the activated silica gel with an aminosilane and a polyfunctional reactant, and the second enzyme layer is covalently bonded to the first layer with a polyfunctional reactant. Third, fourth and more successive enzyme layers may be covalently bonded. The composite has high activity per unit volume, superior stability and good half-life.

20 Claims, 4 Drawing Figures

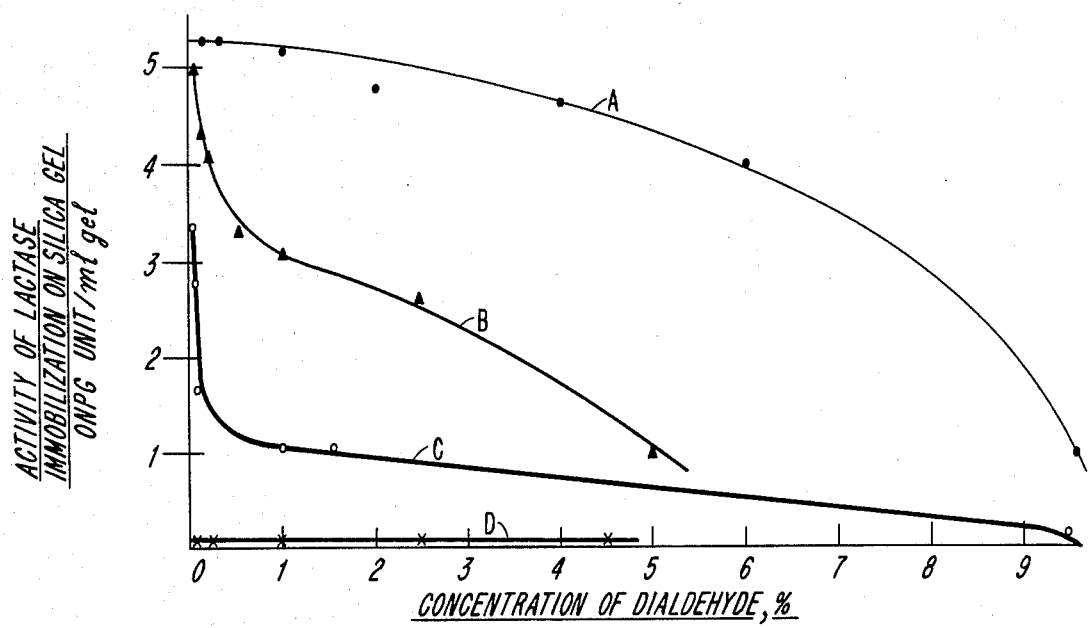

THE DEPENDENCE OF IMMOBILIZED LACTASE ACTIVITY ON THE CONCENTRATION OF DIALDEHYDE SOLUTIONS.
A. - ETHANEDIAL
B - GLUTARALDEHYDE
C - O-PHTHALDIALDEHYDE
D - P-PHTHALDIALDEHYDE
THE SUPPORT MATRIX IS SILICA GEL.

Fig. 1

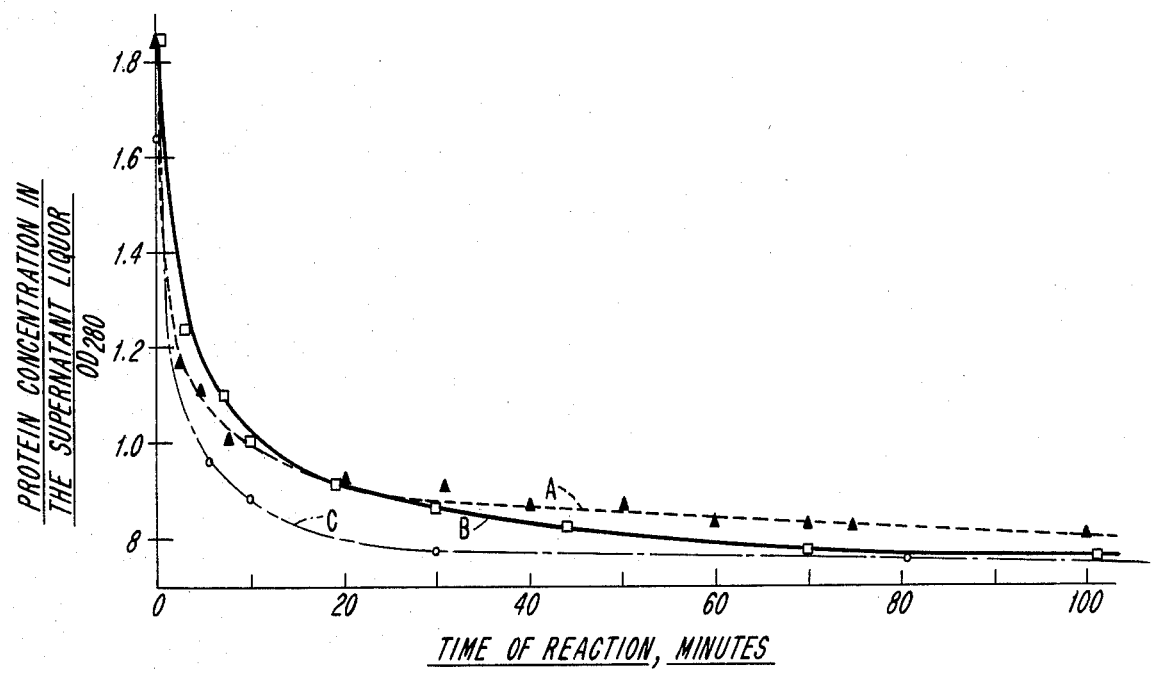

TIME OF REACTION, MINUTES
ENZYME COUPLING KINETICS WITH DIALDEHYDES AS IMMOBILIZING REAGENTS AT ROOM TEMPERATURE.
A - ONE LAYER IMMOBILIZATION WITH GLUTARALDEHYDE
B & C - ONE LAYER AND TWO LAYER IMMOBILIZATION WITH ETHANEDIAL

Fig. 2

THE TEMPERATURE DEPENDENCE OF THE IMMOBILIZED LACTASE ACTIVITY ON ONPG.
THE IMMOBILIZING REAGENT IS ETHANEDIAL AND THE SUPPORT MATRIX IS SILICA GEL.

THE TEMPERATURE STABILITY OF IMMOBILIZED LACTASE ACTIVITY ON ONPG.
THE IMMOBILIZING REAGENT IS ETHANEDIAL AND THE SUPPORT MATRIX IS SILICA GEL.

MULTI-LAYER IMMOBILIZED ENZYME COMPOSITIONS

This is a continuation of application Ser. No. 148,012, filed May 8, 1980, now abandoned.

INTRODUCTION

This invention relates to an immobilized composition of a biologically active material that can be prepared to have an unusually high amount of activity per unit volume. More particularly, the invention relates to an immobilized enzyme composition in which the enzyme is immobilized in novel fashion.

BACKGROUND

Enzymes are proteinaceous catalytic materials that have great industrial potential. Enzymes also are often very expensive materials. They are generally soluble in their respective substrates and except where the conversion product is of great value, recovery of the enzyme for reuse may be difficult or impossible. In some cases, the processing conditions may destroy the enzyme. Where the enzyme is not destroyed, it may be necessary to destroy it, as in some food products, where continued activity would have an unwanted effect.

To avoid these problems, fixed or immobilized enzyme systems have been developed in recent years. Procedures such as adsorption, encapsulation, and covalent bonding are routinely used with many enzymes. The immobilization procedure selected, from the many available, produces a composition that can be used in either batch or continuous processes, but that is most advantageously used in a continuous process for economy.

While the term "insolubilized enzyme" has been used in the past on occasion, as in U.S. Pat. No. 3,519,538, to refer to an enzyme coupled by covalent chemical bonds to an insoluble inorganic carrier, and thus rendered not soluble in water, the term "immobilized" is used herein to refer to such an enzyme, or other biologically active material, fixed to any kind of carrier, i.e., organic or inorganic.

The term "stabilized" is used herein to refer to a biologically active material, such as an enzyme, that has been stabilized against the loss of activity that would otherwise occur because of aging or exposure to an elevated temperature, or use in a reaction as a catalyst.

In the process of immobilizing an enzyme, there are many important practical considerations. There should be as little loss of enzyme activity as possible. The cost of immobilization should be low. The carrier material should be one that does not have a deleterious effect on the action of the enzyme during the process in which it is to be used. The immobilized enzyme should not leak enzyme or any other material into the reaction mixture, especially in food processing applications. The activity of the enzyme should remain high over a long period of operating (reaction) time, generally measured, in industrial processes, as the half-life. In addition, the immobilized enzyme should offer good hydraulic characteristics, to permit reasonable throughput rates. Equally importantly, the immobilized enzyme should be able to withstand reasonable operating temperatures, to permit practical operating rates, with the least feasible loss of activity.

For economy, it is also desirable that recharging of the carrier be possible, to reactivate spent immobilized enzyme, preferably by as simple an operation as possible.

Work in the field has progressed from concern simply with trying to immobilize an enzyme on a water-insoluble carrier to more sophisticated work in which the objective was to produce an immobilized enzyme that would deal successfully with all of the practical considerations mentioned above.

Several United States patents describe advances in the art that are representative of what has been done.

In U.S. Pat. No. 3,519,538, Messing and Weetall describe an immobilized enzyme composition in which the enzyme is covalently coupled to an inorganic carrier through an intermediate silane coupling agent, the silicon portion of the coupling agent being attached to the carrier and the organic portion of the coupling agent being attached to the enzyme. While glass of controlled porosity was the preferred carrier material, a wide variety of inorganic carrier materials, often siliceous, are disclosed as being useful.

In U.S. Pat. No. 3,556,945, Messing disclosed an immobilized enzyme composition which was said to be characterized by no loss of activity because of the immobilization. The enzyme was one having available amine groups, and it was coupled to a porous glass carrier through reactive silanol groups, by means of amine-silicate bonds and by hydrogen bonding.

In U.S. Pat. No. 3,669,841, Miller describes immobilized enzyme compositions in which the enzyme is attached to siliceous materials by a process involving first, the silation of the siliceous carrier, to introduce functional groups, and the linking of the functional groups to an enzyme by means of cross-linking agents. The cross-linking agents identified by Miller include formaldehyde, other monoaldehydes, polyaldehydes, bispropiolates, and disulfonyl halides. In Example 1 of the patent, gamma-aminopropyltrimethoxysilane is reacted with particulate silica, then an enzyme is added with stirring, and then an aqueous formaldehyde solution is added.

Tomb and Weetall in U.S. Pat. No. 3,783,101, describe the covalent coupling of enzyme to a silanated carrier by the use of glutaraldehyde.

In U.S. Pat. No. 3,796,634, Haynes and Walsh describe an immobilized enzyme composition in which the enzyme is said to be adsorbed as a monolayer, enveloping colloidal silica particles. The monolayer is produced by cross-linking the enzyme with a cross-linking agent.

In U.S. Pat. No. 3,836,433, a polyaldehyde is used to fix an enzyme to a gel of an organic material such as, for example, a polyacrylamide or a polysaccharide.

The literature also reports a great many immobilized enzyme compositions and ways in which they may be used. For example, Olsen and Stanley, in the Journal of Agricultural and Food Chemistry, vol. 21, No. 3 (1973), pages 440–445, and in U.S. Pat. No. 3,767,531, describe immobilized enzyme compositions in which lactase and other enzymes are bound to a phenolformaldehyde resin with glutaraldehyde.

Other biologically active materials can also be immobilized for useful purposes. For example, in U.S. Pat. No. 3,839,153, conjugates of biologically active materials, such as human chloriongonadotrophine, insulin, and cortisol, are conjugated with different enzymes respectively by a reaction with glutaraldehyde. The conjugates are useful in immunoassays.

BRIEF SUMMARY OF THE PRESENT INVENTION

In one aspect, the present invention is in a process for preparing novel immobilized compositions of biologically active materials, particularly proteinaceous materials such as, for example, immunoreactants, but especially, of enzymes.

In this process, a suitable carrier material is treated to activate its surface to have residual hydroxyl groups thereon. A hydrolyzable silane having an amine substituent, is then coupled to the hydroxyl groups on the activated surface of the carrier. A polyfunctional coupling agent is then reacted with the amine group of the silane. Preferably, the polyfunctional material is a polyaldehyde or a bis-imidate, but other such materials may be used. Next, after removal of unreacted material, the biologically active material, such as an enzyme, having available amine groups, is reacted with the free (unreacted) aldehyde groups. This step covalently bonds the enzyme or other material to the carrier, without substantial loss of activity.

At this stage, there is a single amount or "layer" of material, such as enzyme, immobilized by covalent bonding to the carrier. The immobilized material, preferably enzyme, has available amine groups, and these are reacted in turn with an additional amount of a polyaldehyde, preferably glyoxal. After washing, additional material, such as enzyme, is added, which covalently bonds through its available amine groups with the unreacted aldehyde groups, to form a covalent bond between the added material and the initially immobilized material.

When the immobilized material is an enzyme, in effect, there are two immobilized enzyme "layers", one covalently bonded to the carrier, and the other covalently bonded to the initially immobilized "layer" of enzyme. The word "layer" is not aptly descriptive; the term is used for convenience and because those skilled in the art will understand it.

The process may be repeated as often as desired, to form a multilayered immobilized composition. This composition is a second aspect of the invention. It can be prepared so as to retain high activity, has high activity per unit volume, and can be prepared to have unusually good thermal stability, good half-life, and practical mechanical strength.

In a preferred embodiment, the carrier material is a finely divided, free-flowing particulate material, most preferably a silica gel, and the immobilized material is the enzyme, lactase (EC 3.2.1.23). One feature of the invention is the use of this immobilized lactase in the treatment of whey, to convert the whey into more useful products.

BRIEF DESCRIPTION OF THE DRAWINGS

In the drawings:

FIG. 1 is a graph plotting the units of activity per ml. of single layer immobilized enzyme composition prepared in accordance with certain embodiments of the invention, where lactase is immobilized on silica gel through the use of each of four different dialdehyde cross-linking reagents, employed at different concentrations for comparative purposes, showing the concentration dependence of the dialdehydes;

FIG. 2 is a graph plotting protein (enzyme) concentration against reaction time in minutes, showing the progress of immobilization and the decrease in enzyme concentration for first layer immobilization of lactase with glutaraldehyde, Curve A, and for first layer and second layer immobilization with glyoxal, Curves B and C respectively;

DETAILED DESCRIPTION OF THE INVENTION

Figure 3:
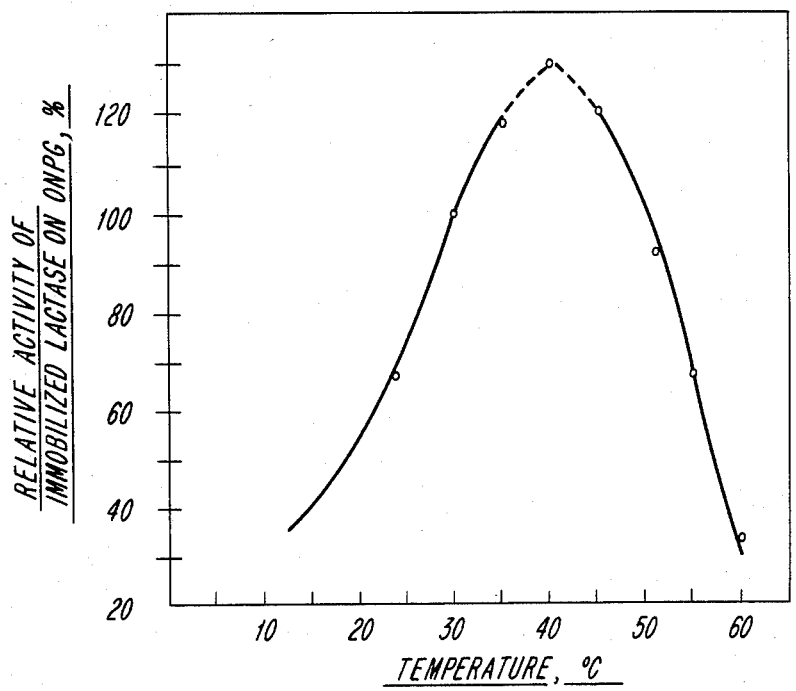
FIG. 3 is a plot of the activity of immobilized lactase on ortho-nitrophenyl galactopyranoside (ONPG) as a substrate, at different temperatures.

To make an immobilized enzyme composition in accordance with the present invention, the carrier material is preferably in particulate form, most preferably finely divided and free-flowing, but in addition, may be in the form of fibers, tubes, sheets, beads, or porous glass. In any form, it should provide a very high surface area per unit volume.

The carrier may be any chemically inert natural or synthetic material, such as, for example, a polymer that is capable of forming a gel in aqueous media. Generally, siliceous materials are preferred. These materials include granulated, fibrous and finely particulate silica and silicates. The carrier material may also be, for example, porous glass, asbestos, diatomaceous earth, wollastonite, fosterite, feldspar, mullite, several different kinds of clay, and in general, any material that has or can be formed to have a shape that makes processing practical in the desired end use, that offers a high surface area per unit volume, and that either has or can be treated to have active hydroxyl groups at its surface that can react with hydrolyzable groups of an organosilane or cyanogen bromide, that acts as a coupling agent.

In a preferred embodiment, a silica gel is treated with a strong acid or a strong base, in order to activate it by generating hydroxyl groups at the surface of the gel particles. The activated carrier is then reacted with a coupling agent, preferably a silane that couples to the carrier at one portion of its molecule, and that provides at a remote part of its molecule a reactive amine group.

The preferred kind of silane coupling agent has the formula:

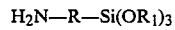

$$H_2N-R-Si(OR_1)_3$$

where R is an alkylene group, and $R_1$, of which there are three per molecule, is preferably alkyl, most preferably lower alkyl, and the three $R_1$ substituents may be the same or different on a given molecule.

In the next step, a suitable amount of a polyfunctional reactant, preferably a polyaldehyde, and most preferably glyoxal, in a suitable solvent medium, is brought into contact with the amine-reactive silica gel or other carrier. In preferred embodiments, this makes the silica gel aldehyde-reactive or aldehyde-functional.

The aldehyde-functional carrier is then mixed with enzyme (or other biologically active material) having available amine groups. The available amine groups of the enzyme react with the free aldehyde groups of the carrier, to immobilize the enzyme on the carrier. The composite is then washed to remove excess unreacted materials.

The immobilized enzyme now consists of a carrier to which a first amount or layer of enzyme is covalently bonded. The enzyme is one having available amine groups. In the next step, this immobilized enzyme composition is reacted with a polyfunctional material, most preferably glyoxal, so that it becomes aldehyde-functional. It is then reacted with a second amount of enzyme, which in turn becomes covalently bonded, this time to the initially immobilized enzyme. This process can then be repeated to add as much enzyme as desired to the composition. Generally not more than 10 layers are practical, and most preferably a total of four layers are applied when the enzyme is lactase and the carrier is silica gel. When proper procedures are employed with careful control over the amount of reactants and the removal of excess reactants, there is relatively little observed loss of enzyme activity.

The reaction of aldehyde and amine groups takes place readily even at low temperatures, so that the reaction can be conducted at 5° C. in solution, and from slight acidity to a moderate pH range. The pK values of the alpha-amino groups in most enzymes and other polypeptides fall in the range from about 7 to about 8. Thus, most enzymes and other such polypeptide materials may be immobilized at a pH that is very close to being neutral, which is a mild condition that sustains activity.

In practicing the present invention, it is important to avoid unwanted cross-linking that may occur. The extent of cross-linking can be limited by careful control over the amount and concentration of cross-linking agent, such as glyoxal, that is employed, and by washing to remove unreacted excess cross-linker as soon as the covalent bonding has had a reasonable opportunity to go to completion.

With proper limitation of the cross-linker and of its reaction, when lactase is immobilized according to the invention in multiple layers on silica gel, using glyoxal as the polyfunctional agent, the amount of enzyme activity retained corresponds to the activity described by the ratio, for a three layer structure, of 100% to 70%–95% to 70%–95%. This ratio relationship is employed as a descriptor of cumulative activity, but at this time it is not known in which layer (if in any single layer) the decrease occurs. Limited cross-linking stabilizes the immobilized enzyme; too much reduces the activity. Some cross-linking, with consequent reduction in activity, seemingly cannot be avoided.

Immobilized multilayered lactase on a silica gel carrier, prepared in accordance with the invention, is generally characterized by advantageously high activity per unit volume; high mechanical and thermal stability; and prolonged half-life.

The invention will now be further illustrated by several specific demonstrations of the practice of preferred embodiments thereof. In this application, all parts and percentages are by weight, and all temperatures in degrees Celsius, unless expressly stated to be otherwise.

EXAMPLE 1

Preparation of Chemically Active Groups on Surface of Support Matrix—Silica Gel

Step A. Preparation of Propylamine Silica Gel 10 g. of silica gel, $(SiO_2)_n$, 35-70 mesh, ASTM, from E. Merck, Darmstadt, Germany, was activated by suspending it in 50 ml of 2% NaOH solution. The mixture was heated and maintained at 40° C. for 1½ hours with occasional gentle stirring. The alkaline solution was then filtered on a plastic frit-funnel, and the gel was suspended in 50 ml of 20% $HNO_3$ solution to neutralize the residual alkali.

The resulting hydrophilic silica gel was then added to 50 ml of 4% gamma-aminopropyl triethoxy silane solution which had been adjusted to pH 5.0 with acetic acid. The gel-silane reagent mixture was heated and maintained at 65°–75° C. for 1½ hours with stirring. The silane solution was then decanted.

The propylamine silica gel product was neutralized with 4% KOH solution to about pH 7.5, then washed exhaustively with distilled water on a plastic frit-funnel, and then vacuum dried for storage. It could be used as is, without drying. This propylamine silica gel product can be used as a carrier for immobilization thereto by covalent bonding, as with a dialdehyde such as glyoxal, of any biologically active compound that has an available amine group, such as enzymes, hormones, immunoreactants, and the like. The general technique is particularly useful for the preparation of an enzyme electrode.

Step B. Preparation of Aldehyde Silica Gel 25 ml of the propylamine silica gel was mixed with 50 ml of 0.1% ethanedial (glyoxal) solution in 0.1M potassium phosphate buffer, pH 8.0, which contains 1% reagent alcohol in a flask, immediately evacuated and filled with $N_2$ gas, then heated to about 40° C. for 1½ hours with occasional gentle shaking. The aldehyde silica gel was then filtered on a plastic frit-funnel, washed with distilled $H_2O$, and immediately vacuum dried for storage. The container was filled with $N_2$ gas to prevent oxidation.

Step C. Preparation of Immobilized Lactase Enzyme on Silica Gel 25 ml of the aldehyde silica gel was added to 50 ml of diluted Lactozym 750L lactase (NOVO Industri AS, Denmark) in 0.1M potassium phosphate—5 mM $MgSO_4$—pH 7.3, the amount of enzyme being in excess of the amount required for coupling. The reaction vessel was immediately evacuated. The reaction proceeded at room temperature for 1 hour with occasional gentle shaking.

The lactase-silica gel product was filtered on a plastic frit-funnel to remove the excess enzyme, and washed with washing buffer (0.02M potassium phosphate, 5 mM $MgSO_4$, pH 7.0). The lactase-silica gel was then suspended in enzyme buffer (0.04M potassium phosphate, 5 mM $MgSO_4$, pH 7.0) and stored at 4° C.

Step D. Multiple Layer Immobilization of Enzyme 25 ml of lactase silica gel (sedimented gel volume) was added to 50 ml of 0.1% ethanedial solution in enzyme buffer (0.1M potassium phosphate, 5 mM $MgSO_4$, pH 7.3) which contained 1% reagent alcohol, and the flask was then evacuated. The mixture was reacted at room temperature for 1½ hours with occasional mild shaking.

The aldehyde-functional enzyme gel was filtered and washed with washing buffer at pH 7.0, then immediately added to 50 ml of diluted Lactozym 750L lactase (20×dilution by volume, NOVO Industri AS, Denmark) solution, again in enzyme buffer (0.1M potassium phosphate, 5 mM $MgSO_4$, pH 7.3). This mixture was reacted about 1 hour at room temperature.

The silica gel carrier, now having two "layers" or applications of lactase immobilized thereon, was filtered and washed with washing buffer at pH 7.0, suspended in enzyme buffer at pH 7.0, and stored at 4° C.

Third, fourth and even more "layers" of enzyme have been immobilized by repeating this same procedure, with relatively little loss in activity.

Step E. Regeneration of Enzyme Silica Gel Activity

After use, spent lactase silica gel, which may retain some relatively low level of lactase activity, can be regenerated to increase and restore its lactase activity by following a similar procedure to that described in Step D. The spent enzyme gel still contains covalently linked proteinaceous material, having available amine groups, which can be reacted with ethanedial, followed by lactase immobilization as in Step D.

EXAMPLE 2

Multiple Enzyme Immobilization

A procedure similar to that in Step D of Example 1 was followed, except that, for the layers of enzyme applied subsequent to the first, lipase (Marshall lipase, Miles Laboratories, Inc.) was used instead of Lactozym 750L.

This immobilized enzyme composition exhibits the enzyme activities of both lactase and lipase. It is therefore useful for the production of lipolyzed cream and butter oil. The controlled-lipolysis of such products can enhance the buttery flavor and/or can be used in a variety of products.

Similarly, the procedure of Step D of Example 1 was followed, except that the enzyme applied, for layers subsequent to the first, was the protease bromelin (Midwest Biochemical Corp. U.S.A.). This immobilized enzyme composition exhibited the enzyme activities of both lactase and protease. It was useful for the hydrolysis of the sugars and proteins in cheese whey.

In similar fashion, following a procedure similar to that in Step D of Example 1, the enzyme employed for application subsequent to the first layer may be a mixture of lipase and protease. The resulting immobilized enzyme composition will exhibit the activity of all three enzymes, that is, of lactase, lipase, and protease. Such a composition is useful in the processing of dairy products for the controlled hydrolysis of lactose, and whey proteins, as well as the controlled lipolysis of lipids for enhanced flavors.

Alternatively, spent immobilized enzyme may be employed as the base on which to immobilize enzymes other than the original enzymes, following generally the procedure of Step E of Example 1.

EXAMPLE 3

Evaluation and Comparison of Different Dialdehydes in Immobilization

The procedure of Example 1 was followed to immobilize lactase on silica gel, with the use of glyoxal as the coupling agent, and for comparative purposes, with the use of other dialdehydes in place of glyoxal.

Four structurally preferred, different dialdehydes were tested for suitability for immobilizing. Their chemical formulae are as follows:

| | | |
|---|---|---|
| ethanedial (glyoxal) | OHC—CHO | |
| n-pentanedial (glutaraldehyde) | OHC—CH$_2$—CH$_2$—CH$_2$CHO | | o-phthaldialdehyde 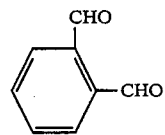

p-phthaldialdehyde 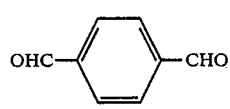

The concentration dependence of the dialdehydes as immobilizing reagents is shown in FIG. 1. The ethanedial appears to be the best one, with highest enzyme activity retention (concentration of ethanedial from about 0.03% to about 1%). The glutaraldehyde and O-phthaldialdehyde are less effective and only comparably effective in a very narrow low concentration range (<0.3%). p-phthaldialdehyde appears to exhibit a very low level of usefulness.

The amount of enzyme and the immobilization reaction kinetics for lactase immobilized on aldehyde silica gel with ethanedial and with glutaraldehyde respectively are somewhat similar. The immobilization time course and the disappearance of enzyme concentration in the supernatant liquid for first layer and second layer immobilization of lactase are shown in FIG. 2.

Figure 4:
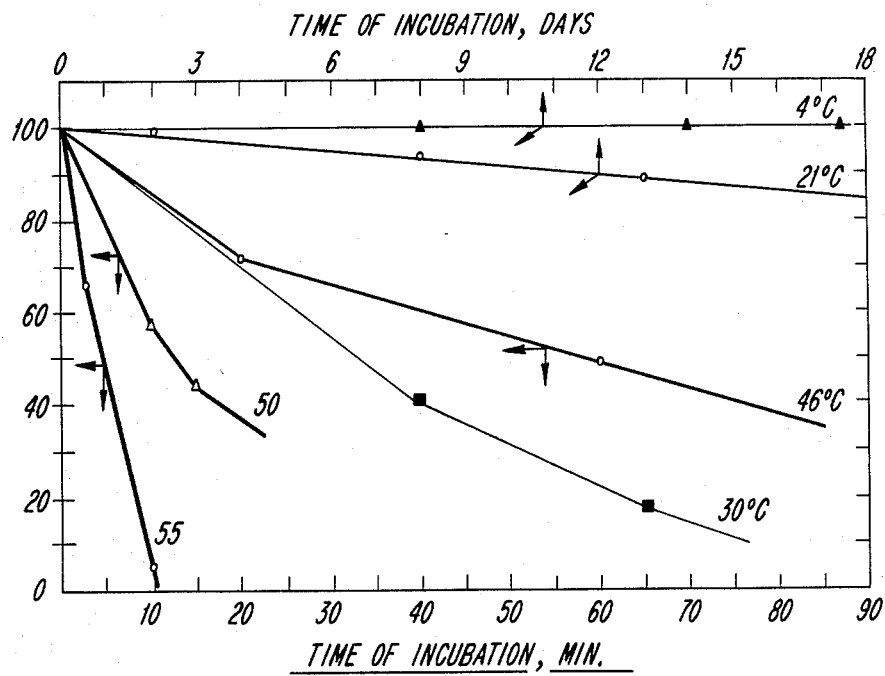
FIG. 4 is a plot of the activity of immobilized lactase against time of incubation with ONPG as a substrate, at different temperatures, the arrows on the several curves indicating the applicable time scale, i.e., whether the time was measured in minutes or days.

The temperature dependence and the temperature stability of the immobilized lactase activity are shown in FIGS. 3 and 4 respectively. The comparison of thermal stability of lactase immobilized with ethanedial and with glutaraldehyde is shown in Tables 1 and 2. The enzyme activity and its active conformational stability can be effectively increased by multi-layer immobilization technique, as shown in Tables 2, 3 and 4.

Again, the relative thermal stability and immobilized lactase activity by layered-immobilization are both significantly improved, and appear, to be much better with ethanedial than with glutaraldehyde. Generally speaking, glutaraldehyde is a good immobilizing reagent, but ethanedial is preferred.

The immobilized enzyme composition of Ex. 1 is useful in treating whey solutions to improve their sweetness. When the immobilized enzyme is a combination of lactase and glucose isomerase, a very sweet product is produced.

DEFINITIONS

Enzyme Activity Unit and Analytical Method

Lactase activity—1 ONPG unit is defined for free enzyme as the hydrolysis of 1 $\mu$mole of ONPG per minute at 30° C. in buffer (0.02M potassium phosphate, $10^{-4}$M M$_n$Cl$_2$, pH 7.0); and for immobilized enzyme, in 0.066 mole potassium phosphate at pH 6.75.

ONPG—ortho-nitrophenyl galactopyranoside.

Lactose determination—use Shaffer-Somogyi micromethod, A.O.A.C., 31.052.

Glucose determination—use Worthington Statzyme Glucose (500 nm).

TABLE 1

Comparison of the temperature stability of immobilized lactase activity with different dialdehydes as immobilizing reagents, respectively. The support matrix is silica gel. Incubation temperature is 50° C.

| Immobilizing Reagent | Immobilized lactase activity after incubation at 50° C. | | | | | |
|---|---|---|---|---|---|---|
| | Mono-layer | | | Double Layer | | |
| | 0 min. | 10 min. | 15 min. | 0 min. | 10 min. | 15 min. |
| Ethanedial | 100% | 30.8% | 17.9% | 100% | 47.9% | 24.0% |
| n-Pentanedial | 100% | 20.6% | 12.6% | 100% | 29.3% | 5.9% |
| o-Phthal-dialdehyde | 100% | 0% | 0% | 100% | 0% | 0% |

NOTE:
1. ONPG was used as lactase substrate.
2. The immobilized lactase activity was determined at its optimum pH.

TABLE 2

Immobilized lactase activity is increased by layering of the enzyme with alkyl dialdehyde, with ethanedial giving the best conformational stability.

| Immobilizing Reagent | Immobilized lactase activity at 30° C., unit/enzyme gel volume | | | | | |
|---|---|---|---|---|---|---|
| | One Layer | | Two Layers | | Three Layers | |
| | ONPG/ml | Percentage | ONPG/ml | % Increase | ONPG/ml | % Increase |
| Ethanedial | | | | | | |
| Run 1 | 4.32 | 100% | 7.68 | 77.8% | — | — |
| Run 2 | 4.32 | 100% | 7.52 | 74.1% | 10.76 | 149.1% |
| Run 3 | 4.32 | 100% | — | — | 10.23 | 138.9% |
| Run 4 | 7.29 | 100% | 12.74 | 75% | 14.86 | 170.2% |
| Run 5 | 5.50 | 100% | 9.60 | 94.7% | — | — |
| glutaraldehyde | | | | | | |
| Run 1 | 3.19 | 100% | — | — | 9.44 | 195.9% |
| Run 2 | 4.93 | 100% | — | — | 10.1 | 104.9% |

Note:
1. ONPG was used as lactase substrate.
2. The immobilized lactase activity was determined at its optimum pH.

TABLE 3

Immobilized lactase enzyme activity is stabilized by enzyme layers which are fixed with ethanedial. Support matrix is silica gel.

| Enzyme Layers | Immobilized lactase activity after incubated at 50° C. | | |
|---|---|---|---|
| | 0 min. | 10 min. | 15 min. |
| 3 layers | 100% | 53.3% | 40.6% |
| 2 layers | 100% | 47.9% | 24.0% |
| 1 layer | 100% | 30.8% | 17.9% |

Note:
1. ONPG was used as lactase substrate.
2. The immobilized lactase activity was determined at its optimum pH.

TABLE 4

Average half-life of immobilized lactase at 50° C. under assay buffer conditions. Lactase was immobilized on silica gel with ethanedial as immobilizing reagent.

| Layers of lactase | Half-life at 50° C. |
|---|---|
| 3 layers | 11.5 min. |
| 2 layers | 8.5 min. |
| 1 layer | 5.5 min. |

NOTE:
1. Immobilized lactase activity was determined at its optimum pH.
2. ONPG was used as lactase substrate.

General

To practice the invention, the siliceous material can be reacted with the organosilane in any convenient manner by contacting the former with the latter to obtain the desired bonding through hydrolyzable groups of the organosilane. Usually the organosilane is dissolved in an inert solvent such as toluene, xylene, or the like, and the resulting solution is then applied to the siliceous material. Aqueous solutions of a soluble silane can also be used.

The amount of organosilane coupling agent employed is dependent upon the nature and surface area of the siliceous material. Usually, at least about 0.01 percent by weight of the organosilane, based on the weight of the siliceous material, is desired. Amounts in the range from about 0.25% to about 2% by weight are preferred.

Suitable organosilanes include substituted organosilanes which can be represented by the formula

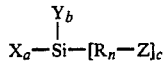

where X is a hydrolyzable group capable of reacting with a hydroxyl group, Y is hydrogen or monovalent hydrocarbon group, R is an alkylene group having from 1 to about 20 carbon atoms, Z is a functional group capable of reacting with a crosslinking agent, n is an integer having a value of 0 or 1, a is an integer having a value of 1 to 3, inclusive, b is an integer having a value of 0 to 2, inclusive, c is an integer having a value of 1 to 3, inclusive, and the sum of a+b+c equals 4.

Examples of suitable X groups include halo, hydroxy, alkoxy, cycloalkoxy, aryloxy, alkoxy-substituted alkoxy such as beta-methoxyethoxy or the like, alkoxycarbonyl, aryloxycarbonyl, alkyl carboxylate, and aryl carboxylate groups, preferably having eight or less carbon atoms.

Examples of suitable Y groups in the above formula are hydrogen, methyl, ethyl, vinyl, isobutyl, and other hydrocarbyl groups, preferably having 10 or less carbon atoms.

The R group in the above formula can be any alkylene group having up to about 20 carbon atoms, and preferably from about 2 to about 18 carbon atoms. Examples of such groups are ethylene, the propylenes, the butylenes, the decylenes, the undecylenes, the octadecylenes, and the like.

The Z groups can be any functional group capable of reacting with the hereinbelow defined crosslinking agent. Examples of such groups are amino, primary and secondary amido, epoxy, isocyanato, hydroxy, alkoxycarbonyl, aryloxycarbonyl, vinyl, allyl, halo such as chloro or bromo, and the like.

Particularly preferred of such functional groups are amino.

Particularly preferred organosilanes for the purposes of this invention are omega-aminoalkyl and aminoaryltrialkoxysilanes such as gamma-aminopropyltrimethoxysilane, aminophenyltriethoxysilane, and the like.

For the purposes of this invention suitable crosslinking agents are dialdehydes, bis-imidoesters, bispropiolates and disulfonyl halides.

Illustrative dialdehydes are glyoxal, glutaraldehyde, malonic aldehyde, succindialdehyde, and the like, preferably containing from 2 to 8 carbon atoms, inclusive.

Illustrative bis-imidoesters are dimethyl adipimidate (DMA), dimethyl suberimidate (DMS), N,N'bis(z-carboximidoester)tartarimide dimethyl ester (CETD), dimethyl 3,3'-dithiobispropionimidate, and the like.

Illustrative bispropiolates are the diol propiolates such as ethylene glycol bispropiolate, propylene glycol bispropiolate, butylene glycol bispropiolate, hexamethylene glycol bispropiolate, decamethylene glycol bispropiolate, cyclohexylene glycol bispropiolate, methylolpropane diol dispropiolate and the like, as well as bisphenol A propiolate, pentaerythritol bispropiolate, and the like.

Illustrative disulfonyl halides are benzene-1,3-disulfonyl chloride, naphthalene-1,5-disulfonylchloride, naphthalene-1,6-disulfonylchloride, naphthalene-2,5-sulfonylchloride, and the like.

The amount of crosslinking agent to be used is dependent principally on the amount of enzyme or enzymes that is desired to be incorporated into the composite. Usually an enzyme crosslinking agent molal ratio is about 1:1 or less. A ratio of about 0.01–0.0001/1.0 is preferred.

The bonding of the enzyme, the crosslinking agent and the organosilane, which is present together with the siliceous material, can be carried out in any convenient inert medium, usually an aqueous medium at pH conditions and temperature which do not tend to inactivate the enzyme. Temperatures above about 60° C. should generally be avoided. The present process is readily carried out at ambient room temperature. The temperature of choice depends, however, mainly on the particular enzyme or mixture of enzymes used. Usually the temperature can range from about −5° C. to about 30° C. A temperature in the range from about 0° C. to about 10° C. is preferred.

Generally the same conditions as mentioned above for immobilization of the initial enzyme layer apply to the immobilization of subsequent enzyme layers.

The dialdehydes are preferred polyfunctional agents for use in the present invention. As FIG. 1 and Table 1 indicate, the dialdehydes are equivalent in performance. Generally, those dialdehydes containing two through four carbon atoms are expected to perform equally well. Dialdehydes having three and four carbon atoms are not readily commercially available at the present time.

Glutaraldehyde (n-pentanedial) is not currently believed t be a simple five carbon molecule. Rather, it is believed to occur, in its commercially available form, as an oligomer, actually a trimer. This makes a substantial difference in the performance of this particular dialdehyde when used in the present invention, since the trimer form would be expected to and apparently does lend itself to the production of cross-linking between enzyme molecules within a given layer. Such intra-layer cross-linking is generally not regarded as desirable, since it apparently tends, based on available data, to reduce activity.

From FIG. 1, the conclusion can readily be drawn that the minimum amount of dialdehyde should be used that is sufficient to produce covalent bonding, and that when more than the minimum is employed, intra-layer cross-linking occurs that reduces enzyme activity.

In developing the data that is reproduced in FIG. 1 the consistent practice was to employ one volume of sedimented immobilized enzyme, on silica gel, with two volumes of the dialdehyde, at whatever concentration of dialdehyde was being used.

Glyoxal (ethanedial) is a superior cross-linker, although the reason for its better performance is not clear. Apparently, from the data plotted in FIG. 1, if the use of glyoxal in excess of that required for coupling leads to intra-layer cross-linking, then the reduction in enzyme activity is much less than is the case with the other dialdehydes.

The choice of cross-linking dialdehyde has some effect upon the way in which the enzyme performs. Thus, the optimum pH of lactase immobilized on silica gel in accordance with the invention is pH 6.75 when the cross-linker is glyoxal, and pH 6.50 when the cross-linker is glutaraldehyde, as compared to pH 7.0 for free lactase. These data suggest that the immobilized lactase retains a more active conformation when coupled with glyoxal than with glutaraldehyde. This comparative data was developed through performance evaluation of immobilized lactase on ONPG at 30° C.

The substrate selected also has a bearing on the performance of immobilized enzyme. Thus, when lactase is immobilized on silica gel, using glyoxal as the coupling agent, the immobilized enzyme generally performs better at a lower pH on lactose than on ONPG.

Immobilized lactase, on silica gel, ordinarily would be used for processing whey at a temperature of about 20° C. (room or ambient temperature) or less, and at the optimum pH for the particular lactase. Thus, for lactase from *Aspergillus niger*, a pH of about 4.5 would be best for enzyme efficiency.

In Table 1, the loss of lactase activity was observed when the immobilized lactase acted on ONPG as a substrate, at 50° C. At this temperature, which is well above the temperature at which the immobilized enzyme would ordinarily be used, the reaction goes forward rapidly, but the loss of enzyme activity is also rapid. The Table 1 data demonstrate that the loss in total activity is less for a double layer immobilizer lactase than for a single layer, indicating that the enzyme has been stabilized by the immobilization procedure.

In Table 2, the units of enzyme activity per unit volume, at 30° C., are compared as between one, two and three layers, and where the coupling agent is glyoxal and glutaraldehyde. The figures for two layers and for three layers report the % increase in activity as compared to a single layer. The activity "density" for the three layer immobilized enzyme is very high, making this material very attractive for use in industrial processes.

Enzyme stability for lactase on silica gel at 50° C. on an ONPG substrate is reported in Table 3, and half-life is reported in Table 4. The three layer material clearly has been thermally stabilized to a very significant extent, and the half-life significantly extended.

From other experiments, it has been determined that beyond about 4 layers, the expense of multiple layering tends to offset the gains, possibly because some cross-linking between layers may occur. Generally, with lactase immobilized on silica gel, activity levels in the range from about 7.5 units/ml. to about 30 units/ml., on ONPG at 30° C., sedimented gel volume, are readily obtained. The lactase enzyme used in practising the invention may be from any desired source; that from *Saccharomyces fragilis* is suitable. When immobilized on silica gel with glyoxal, in two layers, a stability as to activity is ordinarily observed such that at least 20% of the initial activity persists after 7.5 minutes at 50° C. at a pH of about 6.7.

While the dialdehyde cross-linkers, and specifically glyoxal, represent preferred materials, the di-imidoesters and bis-imidates are also preferred materials. The imidoester dimethyl adipimidate approaches glyoxal in its performance as a coupling agent.

The enzymes suitable for immobilization are those having available amine groups. This includes most enzymes of proteinaceous nature. Lactase and glucose isomerase are commercially valuable enzymes that can be immobilized in multiple layers successfully. The same techniques described in Example 1 are useful for producing immobilized glucose isomerase in multiple layers. The multilayer immobilized glucose isomerase is especially useful for producing high fructose corn syrup, by reason of its high activity per unit volume.

Enzymes may be obtained from any suitable source, either vegetable, animal or microbiological. In addition to those mentioned above, the enzymes that act on starch and on sugars are of particular interest. Other enzymes that may be used in accordance with the invention include, for example, cellulase, esterase, nuclease, invertase, amyloglucosidase, and other types of hydrolases; hydrase, pectinases, pepsin, rennin, chymotrypsin, trypsin, urease, agrinase, lysozyme, cytochrome, 11-beta-hydroxylase, and mixtures of these and other enzymes.

In addition, other biologically active materials may be immobilized in multi-layer fashion. The immobilized biologically active material thus obtained has a high level of activity per unit volume that makes the immobilized material very valuable for use in diagnostic assay applications, purification operations, and chromatography applications. For example, many antibodies and antigens have available amine groups. When an antibody or antigen is immobilized in accordance with the present invention, it provides a valuable means for isolating its complementary immunochemical reactant, offering potential for diagnostic assays.

Similarly hormones having available amine groups may be immobilized in multiple layers to provide highly concentrated sources of hormone activity.

Among the features and advantages of the present invention are the very high activity that is obtainable per unit volume, the high mechanical stability, the high thermal stability, and the high operational stability or half-life of the immobilized biologically active materials. In achieving some of these advantages and features, the selection of the cross-linking agent and the extent of cross-linking are important. Particularly outstanding is the performance of multiple layer immobilized enzyme as a catalyst for a variety of reactions for which enzymes are useful.

When the carrier is silica gel, the immobilized enzyme can conveniently be transferred from one container to another by pouring the particulate, free-flowing silica gel particles, which act very much like a liquid. This facilitates use of the immobilized enzyme in conventional reactors such as, for example, pressure leaf filters and upright columns. When lactase is immobilized on silica gel in accordance with the invention, in four layers, a good performance can be obtained in converting lactose to sweeter forms that are more readily assimilable, permitting use of the invention for the processing of milk, whey, and other dairy materials.

While the invention has been described in connection with specific embodiments thereof, it will be understood that it is capable of further modifications, and this application is intended to cover any variations, uses, or adaptations of the invention following in general the principles of the invention and including such departures from the present disclosure as come within known or customary practice within the art to which the invention pertains and as may be applied to the essential features hereinbefore set forth, and within the scope of the appended claims.

What is claimed is:

1. An enzymatically reactive composite having a high surface area per unit volume and having plural sequentially applied amounts of enzyme which comprises an activated silica gel having chemically reactive groups at its surface, said activated silica gel prepared by treating silica gel first with a strong base and then treating the resulting material with a strong acid, a first amount of an enzyme immobilized to said composite by a chemical coupling means comprising an aminosilane covalently bonded to said reactive groups and a first amount of a polyfunctional reactant covalently bonded to said aminosilane and to said first amount of an enzyme and a second amount of the same or a different enzyme immobilized to said composite by a second amount of a polyfunctional reactant covalently bonded to said first amount of enzyme and to said second amount of enzyme, said enzymes substantially retaining their activities.

2. The composite of claim 1 which further comprises a third amount of a same or different enzyme immobilized to said composite by a third amount of a polyfunctional reactant covalently bonded to said second amount of enzyme and to said third amount of enzyme.

3. The composite of claim 1 wherein said first-named enzyme and said second-named enzyme are the same enzyme.

4. The composite of claim 2 wherein said first-named enzyme, said second-named enzyme and said third-named enzyme are the same enzyme.

5. The composite of claim 3 wherein the enzyme is lactase or glucose isomerase.

6. The composite of claim 4 wherein the enzyme is lactase or glucose isomerase.

7. The composite of claim 5 wherein said polyfunctional reactant is ethandial or glutaraldehyde.

8. The composite of claim 6 wherein said polyfunctional reactant is ethandial or glutaraldehyde.

9. An enzymatically active composition of one or more immobilized enzymes comprising an activated silica gel having chemically reactive groups at its surface, said activated silica gel prepared by treating silica gel first with a strong base and then treating the resulting material with a strong acid, and plural, sequentially immobilized amounts of one or more enzymes, said one or more enzymes sequentially immobilized to said silica gel by immobilizing a first amount of a first enzyme by a chemical coupling means comprising an aminosilane covalently bonded to said reactive groups and a first amount of a polyfunctional reactant covalently bonded to said aminosilane and to said first amount of said enzyme and by immobilizing a second amount of the same or a different enzyme by a second amount of a polyfunctional reactant covalently bonded to said first amount of enzyme and to said second amount of enzyme, said enzymes substantially retaining their activities.

10. The composition of claim 9 wherein a third amount of the same or a different enzyme is immobilized by a third amount of a polyfunctional reactant covalently bonded to said second amount of enzyme and to said third amount of enzyme.

11. The composition of claim 9 wherein said first-named enzyme and said second-named enzyme are the same.

12. The composition of claim 11 wherein the enzyme in lactase or glucose isomerase.

13. The composition of claim 9 wherein one of said enzymes is lastase and the other of said enzymes is glucose isomerase.

14. The composition of claim 12 wherein said polyfunctional reactant is ethandial or glutaraldehyde.

15. The composition of claim 13 wherein said polyfunctional reactant is ethandial or glutaraldehyde.

16. An immobilized lactase composition comprising an activated silica gel having chemically reactive groups at its surface, said activated silica gel prepared by treating silica gel first with a strong base and then treating the resulting material with a strong acid, a first amount of lactase immobilized to said silica gel by a chemical coupling means comprising an aminosilane covalently bonded to said reactive groups and a first amount of a polyfunctional reactant covalently bonded to said aminosilane and to said first amount of lactase and a second amount of lactase immobilized to said silica gel by a second amount of a polyfunctional reactant covalently bonded to said first amount of lactase and to said second amount of lactase, each of said amounts of lactase contributing to the lactase activity of the immobilized lactase composition.

17. The composition of claim 16 further comprising a third amount of lactase immobilized to said silica gel by a third amount of a polyfunctional reactant covalently bonded to said second amount of lactase and to said third amount of lactase.

18. The composition of claim 17 which further comprises a fourth amount of lactase immobilized to said silica gel by a fourth amount of a polyfunctional reactant covalently bonded to said third amount of lactase and to said fourth amount of lactase.

19. The composition of claim 16, wherein said polyfunctional reactant is ethanedial or glutaraldehyde.

20. The composition of claim 17, wherein said polyfunctional reactant is ethanedial or glutaraldehyde.

* * * * *